United States Patent
Serino et al.

(10) Patent No.: US 11,898,987 B2
(45) Date of Patent: Feb. 13, 2024

(54) SAW-BASED HYDROGEL TESTING FOR DETECTING VIRUSES OR OTHER ANTIGENS

(71) Applicant: Raytheon Company, Waltham, MA (US)

(72) Inventors: Anthony Serino, Northborough, MA (US); Miles T. Rogers, Watertown, MA (US); James A. Bilotto, Beaver, PA (US); William J. Cottrell, Melrose, MA (US)

(73) Assignee: Raytheon Company, Tewksbury, MA (US)

( * ) Notice: Subject to any disclaimer, the term of this patent is extended or adjusted under 35 U.S.C. 154(b) by 814 days.

(21) Appl. No.: 17/017,398

(22) Filed: Sep. 10, 2020

(65) Prior Publication Data

US 2022/0074894 A1 Mar. 10, 2022

(51) Int. Cl.
*G01N 29/02* (2006.01)
*G01N 29/14* (2006.01)
*G01N 33/559* (2006.01)
*G01N 33/569* (2006.01)

(52) U.S. Cl.
CPC ........... *G01N 29/022* (2013.01); *G01N 29/14* (2013.01); *G01N 33/559* (2013.01); *G01N 33/56983* (2013.01)

(58) Field of Classification Search
CPC .... G01N 29/022; G01N 29/14; G01N 29/036; G01N 2291/025; G01N 2291/0256; G01N 2291/0423; G01N 33/559; G01N 33/56983
See application file for complete search history.

(56) References Cited

U.S. PATENT DOCUMENTS

| 6,680,646 B2* | 1/2004 | Disney | H02M 1/08 |
| | | | 327/566 |
| 6,827,281 B2 | 12/2004 | Edmonson et al. | |
| 6,837,097 B2* | 1/2005 | Cunningham | G01N 29/22 |
| | | | 422/69 |

(Continued)

FOREIGN PATENT DOCUMENTS

CA 2520812 A1 3/2006

OTHER PUBLICATIONS

Stubbs et al., "P1-39: Vapor Phase SAW Immunoassay Sensors", Proceedings of IEEE Sensors 2002, Jun. 2002, 4 pages.

(Continued)

*Primary Examiner* — Emily P Pham (57) ABSTRACT

An apparatus includes a surface acoustic wave (SAW) sensor. The SAW sensor includes a piezoelectric substrate. The SAW sensor also includes first and second interdigitating transistors over the piezoelectric substrate. The first interdigitating transistor is configured to convert an input electrical signal into an acoustic wave. The second interdigitating transistor is configured to convert the acoustic wave into an output electrical signal. The piezoelectric substrate is configured to transport the acoustic wave. The SAW sensor further includes a detection layer over the piezoelectric substrate and positioned at least partially between the first and second interdigitating transistors. The detection layer includes (i) antibodies configured to bind to one or more biological analytes and (ii) a hydrogel layer over the antibodies.

20 Claims, 3 Drawing Sheets

(56) References Cited

U.S. PATENT DOCUMENTS

| | | | |
|---|---|---|---|
| 6,967,428 | B2 | 11/2005 | Edmonson et al. |
| 7,053,524 | B2 | 5/2006 | Edmonson et al. |
| 7,229,821 | B1 | 6/2007 | Edmonson et al. |
| 7,413,892 | B2* | 8/2008 | Hunt .................... G01N 29/022 436/524 |
| 7,451,649 | B2 | 11/2008 | Edmonson et al. |
| 7,473,551 | B2 | 1/2009 | Warthoe |
| 7,608,978 | B2 | 10/2009 | Edmonson et al. |
| 7,650,788 | B2 | 1/2010 | Edmonson et al. |
| 7,651,843 | B2 | 1/2010 | Stubbs et al. |
| 7,771,987 | B2 | 8/2010 | Edmonson et al. |
| 8,168,424 | B2 | 5/2012 | Edmonson et al. |
| 8,420,382 | B2 | 4/2013 | Edmonson et al. |
| 10,031,135 | B2* | 7/2018 | Larson .................. C12Q 1/6825 |
| 10,291,199 | B2* | 5/2019 | McIntyre ........... H03H 9/02275 |
| 10,538,734 | B2* | 1/2020 | Lauraeus ............... C12N 11/12 |
| 11,616,485 | B2* | 3/2023 | Azizi ................... H03H 9/6483 455/232.1 |
| 2005/0112358 | A1* | 5/2005 | Potyrailo ............... B82Y 30/00 428/522 |
| 2008/0142366 | A1 | 6/2008 | Tamirisa et al. |
| 2014/0228249 | A1* | 8/2014 | Chilkoti ........... G01N 33/54353 506/13 |
| 2019/0128853 | A1* | 5/2019 | Wright .................... G01N 29/30 |
| 2019/0187105 | A1* | 6/2019 | Ram .................. G01N 29/2462 |
| 2019/0197082 | A1 | 6/2019 | Edmonson |

OTHER PUBLICATIONS

Lee et al., "Vapor Phase Detection of Plastic Explosives Using a SAW Resonator Immunosensor Array", 2005 IEEE Sensors, Oct. 2005, 4 pages.
Stubbs et al., "Molecular Recognition for Electronic Noses Using Surface Acoustic Wave Immunoassay Sensors", IEEE Sensors Journal, vol. 2, No. 4, Aug. 2002, 7 pages.
International Search Report and Written Opinion of the International Searching Authority dated Oct. 26, 2021 in connection with International Patent Application No. PCT/US2021/044334, 12 pages.
Furukawa et al., "Evidence Supporting Transmission of Severe Acute Respiratory Syndrome Coronavirus 2 While Presymptomatic or Asymptomatic," Emerging Infectious Diseases, vol. 26, No. 7, Jul. 2020, 6 pages.
Moghadas et al., "The implications of silent transmission for the control of COVID-19 outbreaks," www.pnas.org, Jul. 2020, 3 pages.
Salvatori et al., "SARS-CoV-2 Spike Protein: an optimal immunological target for vaccines," Journal of Translational Medicine, vol. 18, No. 1, Jun. 2020, 3 pages.
Stubbs et al., "Investigation of Cocaine Plumes Using Surface Acoustic Wave Immunoassay Sensors," Analytical Chemistry, Sep. 2003, 5 pages.
Long et al., "Clinical and immunological assessment of asymptomatic SARS-CoV-2 infections," Nature Medicine, Jun. 2020, 12 pages.
Riediker et al. "Estimation of SARS-CoV-2 emissions from non-symptomatic cases," medRxiv, May 2020, 18 pages.
Bar-On et al., "SARS-CoV-2 (Covid-19) by the numbers," eLife, Mar. 2020, 4 pages.
Neuman et al., "Supramolecular Architecture of Severe Acute Respiratory Syndrome Coronavirus Revealed by Electron Cryomicroscopy," Journal of Virology, vol. 80, No. 16, Aug. 2006, 11 pages.
McDevitt et al., "Development and Performance Evaluation of an Exhaled-Breath Bioaerosol Collector for Influenza Virus," Aerosol Science and Technology, Jan. 2013, 8 pages.
Ladhani et al., "Electrostatic Sampling of Patient Breath for Pathogen Detection: A Pilot Study," Frontiers in Mechanical Engineering, Jun. 2020, 7 pages.
Wilson, "Review of Electronic-nose Technologies and Algorithms to Detect Hazardous Chemicals in the Environment," Procedia Technology, vol. 1, Jan. 2012, 11 pages.
Behera et al., "Electronic Nose: a non-invasive technology for breath analysis of diabetes and lung cancer patients," Journal of Breath Research, vol. 13, No. 2, Mar. 2019, 4 pages.
Cellini et al., "Potential Applications and Limitations of Electronic Nose Devices for Plant Disease Diagnosis," Sensors, vol. 17, No. 11, Nov. 2017, 13 pages.
Zhou et al., "Rapid breath analysis for acute respiratory distress syndrome diagnostics using a portable two-dimensional gas chromatography device," Analytical and Bioanalytical Chemistry, Aug. 2019, 13 pages.
"BACtrack Select, S80 Breathalyzer", Owner's Manual, Medical Device Depot, Inc., 2020, 10 pages.
Amineh et al., "Dynamic Range of SAW Sensors Regarding Electrical Constraints", Jan. 2005, 4 pages.
"File: Smoke detector.JPG", Wikimedia Commons, Oct. 2007, 4 pages.
Mujahid et al., "Surface Acoustic Wave (SAW) for Chemical Sensing Applications of Recognition Layers", Sensors, Nov. 2017, 26 pages.

\* cited by examiner

SAW-BASED HYDROGEL TESTING FOR DETECTING VIRUSES OR OTHER ANTIGENS

TECHNICAL FIELD

This disclosure relates generally to sensing devices. More specifically, this disclosure relates to surface acoustic wave (SAW)-based hydrogel testing for detecting viruses or other antigens.

BACKGROUND

The transmission of the SARS-CoV-2 (COVID-19) virus or other diseases through respiratory droplets poses a significant challenge to society. Reducing the spread of respiratory diseases requires the ability to quickly detect the presence of those diseases in a rapid and noninvasive manner. However, current tests for the SARS-CoV-2 virus often rely on directly sampling bodily fluids (such as nasopharyngeal aspirate or saliva) from patients and sending those samples to laboratories, where the samples are then processed and finally tested. Unfortunately, this can be an extremely slow process, and these tests are often performed on symptomatic individuals and miss cases of diseases spread through asymptomatic or pre-symptomatic individuals. As a result, this creates a significant burden on the public health infrastructure and is highly insufficient in reducing the spread of the respiratory diseases.

SUMMARY

This disclosure provides for surface acoustic wave (SAW)-based hydrogel testing for detecting viruses or other antigens.

In a first embodiment, an apparatus includes a SAW sensor. The SAW sensor includes a piezoelectric substrate. The SAW sensor also includes first and second interdigitating transistors over the piezoelectric substrate. The first interdigitating transistor is configured to convert an input electrical signal into an acoustic wave. The second interdigitating transistor is configured to convert the acoustic wave into an output electrical signal. The piezoelectric substrate is configured to transport the acoustic wave. The SAW sensor further includes a detection layer over the piezoelectric substrate and positioned at least partially between the first and second interdigitating transistors. The detection layer includes (i) antibodies configured to bind to one or more biological analytes and (ii) a hydrogel layer over the antibodies.

In a second embodiment, a system includes multiple SAW sensors. Each SAW sensor includes a piezoelectric substrate. Each SAW sensor also includes first and second interdigitating transistors over the piezoelectric substrate. The first interdigitating transistor is configured to convert an input electrical signal into an acoustic wave. The second interdigitating transistor is configured to convert the acoustic wave into an output electrical signal. The piezoelectric substrate is configured to transport the acoustic wave. Each SAW sensor further includes a detection layer over the piezoelectric substrate and positioned at least partially between the first and second interdigitating transistors. The detection layer includes (i) antibodies and (ii) a hydrogel layer over the antibodies. The antibodies of at least one of the SAW sensors are configured to bind to one or more biological analytes.

In a third embodiment, a method includes providing a flow of air to one or more SAW sensors and detecting one or more biological analytes in the flow of air using the one or more SAW sensors. At least one of the SAW sensors includes a piezoelectric substrate, first and second interdigitating transistors over the piezoelectric substrate, and a detection layer over the piezoelectric substrate and positioned at least partially between the first and second interdigitating transistors. The first interdigitating transistor is configured to convert an input electrical signal into an acoustic wave. The second interdigitating transistor is configured to convert the acoustic wave into an output electrical signal. The piezoelectric substrate is configured to transport the acoustic wave. The detection layer includes (i) antibodies configured to bind to the one or more biological analytes and (ii) a hydrogel layer over the antibodies.

Other technical features may be readily apparent to one skilled in the art from the following figures, descriptions, and claims.

BRIEF DESCRIPTION OF THE DRAWINGS

For a more complete understanding of this disclosure, reference is made to the following description, taken in conjunction with the accompanying drawings, in which.

DETAILED DESCRIPTION

FIGS. 1 through 6, described below, and the various embodiments used to describe the principles of the present disclosure are by way of illustration only and should not be construed in any way to limit the scope of the disclosure. Those skilled in the art will understand that the principles of the present disclosure may be implemented in any type of suitably arranged device or system.

As noted above, the transmission of the SARS-CoV-2 (COVID-19) virus or other diseases through respiratory droplets poses a significant challenge to society. Reducing the spread of respiratory diseases requires the ability to quickly detect the presence of those diseases in a rapid and noninvasive manner. However, current tests for the SARS-CoV-2 virus often rely on directly sampling bodily fluids (such as nasopharyngeal aspirate or saliva) from patients and sending those samples to laboratories, where the samples are then processed and finally tested. Unfortunately, this can be an extremely slow process, and these tests are often performed on symptomatic individuals and miss cases of diseases spread through asymptomatic or pre-symptomatic individuals. As a result, this creates a significant burden on the public health infrastructure and is highly insufficient in reducing the spread of the respiratory diseases.

This disclosure provides platforms that support immunosensor designs configured to rapidly detect the presence of one or more aerosol viruses or other antigens. Each platform uses at least one surface acoustic wave (SAW)-based sensor that is functionalized with antibodies specific for one or more antigens, such as the SARS-CoV-2 antigen (like its viral spike protein). A hydrogel scaffold supports the antibodies for use in a non-aqueous environment. As aerosol particles (such as respiratory droplets) come into contact with the hydrogel, the contents of the particles diffuse through and interact with the antibodies. Due to the highly specific nature of antibodies, only a specific antigen will interact with the corresponding antibody, and this interaction occurs immediately upon the antigen meeting the antibody. This interaction also changes the oscillation frequency of the SAW-based sensor, which enables detection of the oscillation frequency change and therefore detection of the specific antigen.

In this way, these platforms can quickly detect the presence of individuals shedding viruses like SARS-CoV-2 or other antigens, including asymptomatic and pre-symptomatic individuals, in a non-contact manner. This helps to reduce or eliminate the need to rely on slow contact-based testing and lagging or inconsistent reports from healthcare providers. Also, this approach can be used to create highly-specific sensors that are able to detect particular diseases with limited or no direct interactions with users. Further, this approach can provide rapid results (such as within seconds) and can be compatible with any suitable viral collection technique (such as from breathalyzer masks to wide-area environmental sampling). In addition, this approach does not depend on complex computation or modeling, and this approach supports the use of an extensible platform that only requires a new antibody in order to support the detection of an additional biological threat.

Figure 1:
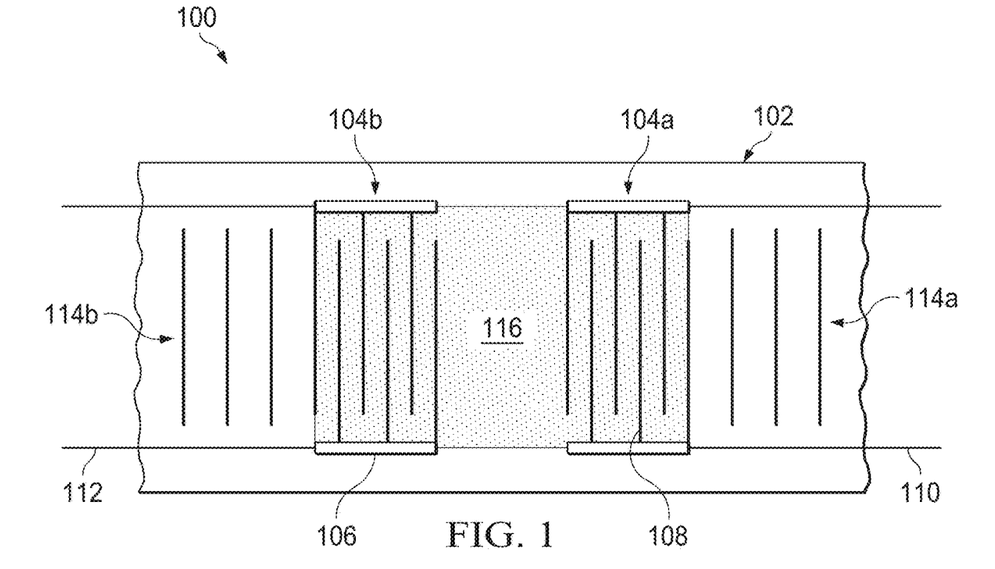
FIGS. 1 through 3 illustrate an example surface acoustic wave (SAW)-based hydrogel sensor for use in detecting viruses or other antigens in accordance with this disclosure.
Figure 2:
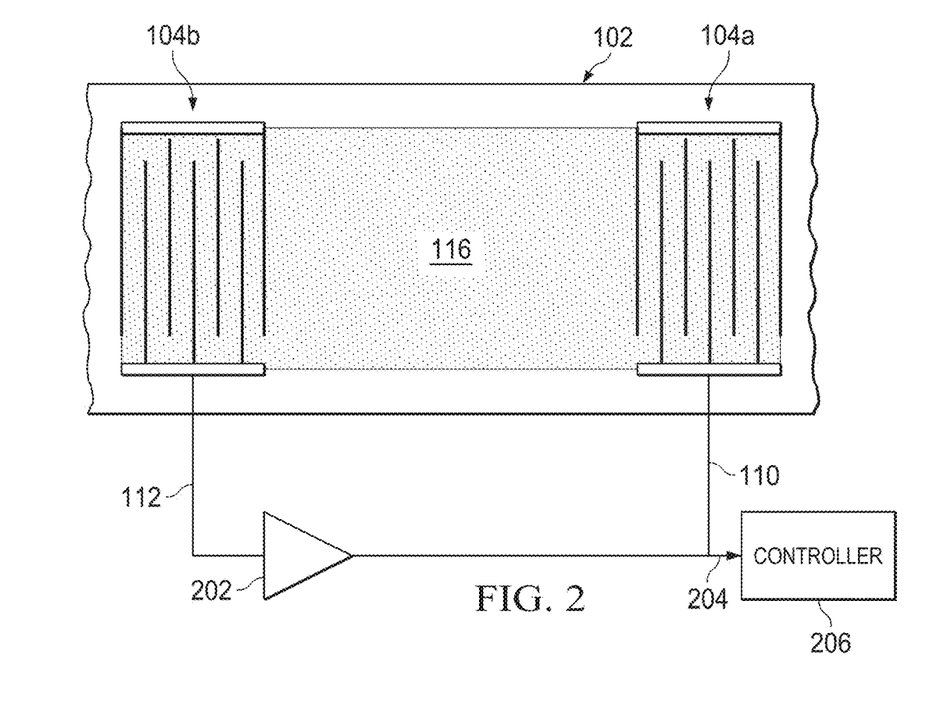
Figure 3:
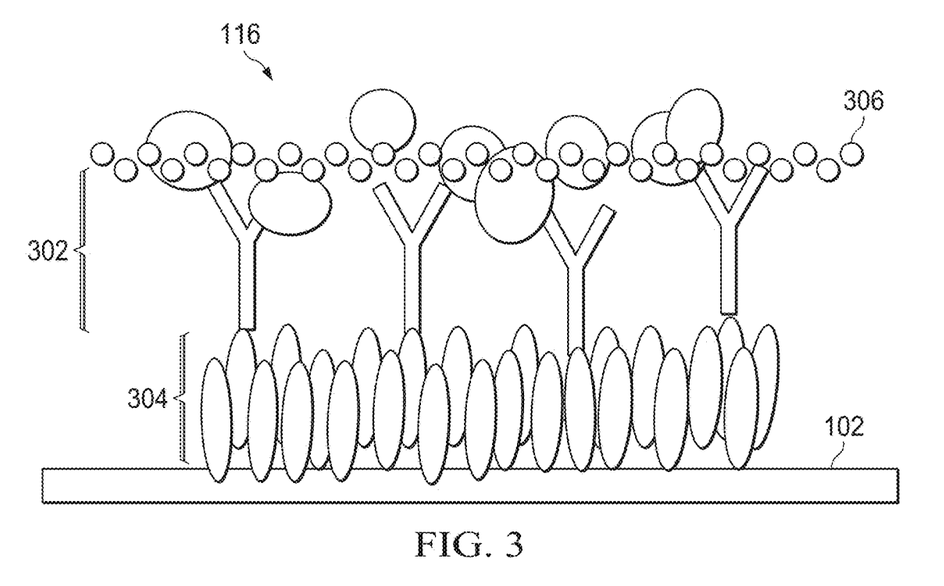

FIGS. 1 through 3 illustrate an example SAW-based hydrogel sensor 100 for use in detecting viruses or other antigens in accordance with this disclosure. As shown in FIG. 1, the sensor 100 includes a piezoelectric substrate 102, which generally represents a structure in or on which other components of the sensor 100 are carried. The piezoelectric substrate 102 may be formed from any suitable piezoelectric material(s), such as quartz. As a particular example, the piezoelectric substrate 102 may be formed using Y-rotated, X-propagating (ST-X) quartz. The piezoelectric substrate 102 may also be formed in any suitable manner, such as by cutting and polishing the piezoelectric material. The piezoelectric substrate 102 may have any suitable size, shape, and dimensions.

Two interdigitating transistors (IDTs) 104a-104b are positioned over the piezoelectric substrate 102. Each interdigitating transistor 104a-104b includes two bases 106 and two sets of conductive fingers 108. The bases 106 are positioned opposite each other, and each conductive finger 108 is electrically coupled to one of the bases 106 and extends towards the other of the bases 106. The conductive fingers 108 are also interleaved or interdigitated such that the conductive fingers 108 are electrically coupled to the bases 106 in an alternating manner. Each interdigitating transistor 104a-104b may be formed from any suitable material(s), such as one or more metals like aluminum. Each interdigitating transistor 104a-104b may also be formed in any suitable manner, such as by depositing and etching metal or other material(s). Each base 106 and each conductive finger 108 of the interdigitating transistors 104a-104b may have any suitable size, shape, and dimensions. Each interdigitating transistor 104a-104b may include any suitable number of conductive fingers 108 and any suitable spacing between its conductive fingers 108.

An input port 110 is coupled to the interdigitating transistor 104a, and an output port 112 is coupled to the interdigitating transistor 104b. During operation, a radio frequency (RF) signal or other electrical signal can be applied to the input port 110, and the interdigitating transistor 104a converts the electrical signal into an acoustic wave. The acoustic wave travels across the substrate 102 to the interdigitating transistor 104b, which converts the acoustic wave into an RF signal or other electrical signal that is provided via the output port 112.

Two sets of reflectors 114a-114b are positioned over the piezoelectric substrate 102 such that the interdigitating transistors 104a-104b are located between the reflectors 114a-114b. The reflectors 114a-114b operate to reflect parts of the acoustic wave that is directed towards the edges of the substrate 102 back towards an interior of the substrate 102, thereby forming a resonant acoustic cavity. The interdigitating transistors 104a-104b and the reflectors 114a-114b cooperate to generate an acoustic standing wave within the resonant acoustic cavity when an input signal is applied to the input port 110, Each reflector 114a-114b may be formed from any suitable material(s), such as one or more metals. Each reflector 114a-114b may also be formed in any suitable manner, such as by depositing and etching metal or other material(s). Each reflector 114a-114b may have any suitable size, shape, and dimensions. Each set of reflectors 114a-114b may include any suitable number of reflectors and any suitable spacing between its reflectors.

In order to support the sensing of one or more viruses or other antigens, the sensor 100 includes a detection layer 116, which is positioned over the piezoelectric substrate 102 and within and between the interdigitating transistors 104a-104b. The detection layer 116 is configured to detect the presence of one or more viruses or other antigens as described below. Note that the detection layer 116 is shown in FIG. 1 as extending across the collections of conductive fingers 108 of the interdigitating transistors 104a-104b. This helps to reduce or minimize the amount of bare substrate material in the cavity region of the sensor 100. This also helps achieve a more uniform distribution of biomolecules in the SAW resonator's most sensitive region.

As shown in FIG. 2, the input port 110 and output port 112 are coupled to an oscillator circuit 202, which is shown generically here as an amplifier. Note that the reflectors 114a-114b are omitted here and that the interdigitating transistors 104a-104b are shown in simplified form here for ease of illustration. The oscillator circuit 202 generally represents a free-running oscillator that causes the sensor 100 to produce an acoustic wave, and the interdigitating transistor 104b feeds its output back into the oscillator circuit 202. The result is that the acoustic wave has a specified frequency, and the frequency can then become lower as viruses or other antigens bind to the detection layer 116. An output 204 of the oscillator circuit 202 represents the output of the SAW-based sensor 100 and can be provided to a controller 206 for processing. The oscillator circuit 202 includes any suitable structure configured to cause a SAW-based sensor 100 to generate an output at a specified frequency. For instance, the oscillator circuit 202 may include a first matching circuit, a phase shifter, an amplifier, an attenuator, and a second matching circuit coupled in series from the output port 112 to the input port 110. Note, however, that this disclosure is not limited to any particular implementation of the oscillator circuit 202.

The use of the detection layer 116 in the SAW-based sensor 100 allows an immediate translation of a biological detection event into an electrical signal. That is, the detection layer 116 includes antibodies for at least one virus or other antigen to be detected. Without any antigens present, the output 204 of the SAW-based sensor 100 may have a specified frequency. As antibodies in the detection layer 116 bind to antigens, the frequency of the acoustic wave produced in the SAW-based sensor 100 decreases, which decreases the oscillator frequency and changes the output 204 of the SAW-based sensor 100. When at least one specific virus or other antigen binds to the antibodies of the detection layer 116 in a suitable quantity to change the frequency of the output 204 by at least some threshold amount, this can be sensed by the controller 206 and used as an indicator that the at least one specific virus or other antigen is present.

The controller 206 processes the output of the SAW-based sensor 100 in order to detect when an adequate number of viruses or other antigens have bound to the antibodies of the detection layer 116 in order to change the oscillating frequency of the sensor 100. For example, the controller 206 may determine if the frequency of the output of the SAW-based sensor 100 has dropped by at least a specified threshold amount. Note that the specific threshold used here can vary based on various factors, such as the desired amount of viruses or other antigens to bind to the detection layer 116. In some cases, for instance, it might take about one thousand virus particles to bind to the detection layer 116 in order to change the frequency of the sensor 100 by about 3 Hertz (Hz). Since a person may have a much higher number of virus particles or other antigens in his or her breathe, a larger frequency change may be used as an indicator of the presence of the viruses or other antigens. Also note that each virus or other antigen might actually be able to bind to multiple antibodies in the detection layer 116, such as when different instances of spike proteins of the SARS-CoV-2 virus can bind to different instances of an antibody in the detection layer 116. This may allow a larger change in the frequency of the SAW-based sensor 100 to be detected based on fewer antigens. Upon the detection of the presence of a specific antigen, the controller 206 may take any suitable action(s), such as triggering an audible or visual alert. The controller 206 may also provide a graphical or other output identifying the change in the frequency of the sensor 100 over time.

The controller 206 includes any suitable structure configured to receive and use outputs of a SAW-based sensor 100. For example, the controller 206 may include processing or other circuitry configured to sense when the frequency output by the SAW-based sensor 100 changes by at least a threshold amount or falls below a threshold value. In some embodiments, the SAW-based sensor 100 may be placed on a first circuit board, and the controller 206 may be placed on a second circuit board that can be coupled to the first circuit board via a Universal Serial Bus (USB) connector or other connector. Note that the controller 206 may be used with one SAW-based sensor 100 or with multiple SAW-based sensors 100.

Some SAW-based designs have been proposed to detect small molecules, such as trace molecules of cocaine or explosives like trinitrotoluene (TNT). These molecules can have molecular weights of 80 daltons (Da) to 50 kilo-daltons (kDa). However, viruses and other antigens typically have much larger molecular weights, such as when viral particles can reach the mega-dalton (MDa) range. As a particular example, the SARS-CoV-2 virus can have a mass of about 1,000 MDa and a diameter of about 100 nanometers (nm). Moreover, the SAW-based sensor 100 may be deployed to operate by receiving an air flow and not a liquid flow. As a result, the detection layer 116 can allow for rapid diffusion of particles with large molecular weights while still sufficiently supporting and hydrating antibodies used to detect antigens.

As shown in FIG. 3, the detection layer 116 includes a layer of antibodies 302. Each of the antibodies 302 can be used to bind to a specific antigen. The specific antibodies 302 used in the sensor 100 can vary as needed or desired. For example, in some embodiments, a single type of antibody 302 may be used to sense a single type of antigen in each sensor 100, and multiple sensors 100 may be used to sense the same antigen or different antigens. Any suitable antibodies 302 may be used in the sensor 100 to identify any desired antigen(s). As particular examples, the antibodies 302 may be used to detect SARS-CoV (which is associated with severe acute respiratory syndrome coronavirus), SARS-CoV-2 (which is associated with COVID-19), MERS-CoV (which is associated with Middle East Respiratory Syndrome), or hemagluttinin or neuraminidase (which are associated with influenza).

The antibodies 302 are immobilized on the piezoelectric substrate 102 using a layer of cross-linkers 304. The cross-linkers 304 help to hold the antibodies 302 on the surface of the piezoelectric substrate 102. Any suitable cross-linkers 304 can be used here, and the specific cross-linkers 304 used can vary depending on the material(s) forming the substrate 102 and the antibodies 302 to be immobilized. In some embodiments, for example, the cross-linkers 304 represent a layer of "protein A", which is a protein originally discovered in the cell walls of the bacteria *Staphylococcus aureus* (commonly found in the upper respiratory tract and on the skin).

A thin hydrogel layer 306 (also called a hydrogel scaffold) is placed over the antibodies 302. The hydrogel layer 306 support the use of the antibodies 302 in a non-aqueous environment. The hydrogel layer 306 includes a collection of polymer chains linked in a three-dimensional network. The hydrophilic nature of the polymers allows the hydrogel layer 306 to contain a high concentration of water without dissolving or falling apart and to retain the water over a prolonged period of time. This high concentration of water supports and hydrates the antibodies 302, allowing them to maintain their specificity for an antigen of interest. Here, one or more antigens of interest can diffuse through the hydrogel layer 306 in order to interact with and bind to the antibodies. The hydrogel layer 306 may support the use of antibodies 302 for any suitable length of time. In some embodiments, for example, the hydrogel layer 306 may last for up to a week or more at 40% relative humidity (RH).

In some embodiments, a formulation of the hydrogel layer 306 for use with a specific type of antibody can be determined as follows. Note, however, that the following details are examples only, and a hydrogel formulation can be determined in any other suitable manner. In order to determine an appropriate hydrogel formulation and concentration over a specified range of particle sizes, commercially-available biotin-labeled microspheres of diameters from 10 nm to 10 micrometers (μm) can be functionalized with a streptavidin conjugated fluorophore, such as fluorescein or rhodamine 6G (R6G). A surface of the SAW-based sensor 100 can be functionalized with an antibody specific to the fluorophore using protein A. After functionalization, the surface of the SAW-based sensor 100 can be covered in a thin layer 306 of hydrogel, where different formulations of the hydrogel can be created as described below. Testing can be performed by liquid injection using a known concentration of functionalized microspheres and/or by nebulizing a known concentration of microspheres, such as by using a Collison nebulizer in a calm air chamber. A determination can then be made which formulation(s) of the hydrogel adequately bind to the microspheres. The testing here can be used to identify a viable formulation for the hydrogel layer 306.

Some formulations can involve the use of agarose hydrogels with concentrations ranging from 0.2% agarose to 5% agarose weight by volume. Hydrogels can be created by dissolving an appropriate amount of powdered agarose into ultrapure water (pH 7) or phosphate buffered saline (PBS, pH 7.4), boiling the solution, and allowing it to cool to slightly above the gel point before pipetting onto the surface of the SAW-based sensor 100.

Other formulations can involve the use of polyacrylamide hydrogels at concentrations ranging from 1% to 15% polyacrylamide. Both Bis-Tris and Tris-Glycine acrylamide solutions can be formulated and tested. Hydrogels can be formulated by diluting a commercial 30% stock solution into a Tris buffer to achieve a final pH of 7. Other common buffers such as 3-(N-morpholino)propanesulfonic acid (MOPS), 4-(2-hydroxyethyl)-1-piperazineethanesulfonic acid (HEPES), and 2-(N-morpholino)ethanesulfonic acid (MES) may also be formulated and tested at neutral pH. After diluting the polyacrylamide to a desired solution and degassing, a gel can be crosslinked using tetramethylethylenediamine (TEMED) and ammonium persulfate (APS). Before crosslinking is completed, a thin layer of the gel can be used to coat the surface of the SAW-based sensor 100.

Still other formulations can involve the use of guar gum hydrogels with concentrations ranging from 0.2% guar gum to 10% guar gum weight by volume. A desired amount of guar gum can be dissolved in 1% glutaraldehyde and used to coat the surface of the SAW-based sensor 100 before completely gelling.

Although FIGS. 1 through 3 illustrate one example of a SAW-based hydrogel sensor 100 for use in detecting viruses or other antigens, various changes may be made to FIGS. 1 through 3. For example, the sizes, shapes, and dimensions of the sensor 100 and its various components may vary as needed or desired. Also, the layout and arrangement of components may vary as needed or desired.

Figure 4:
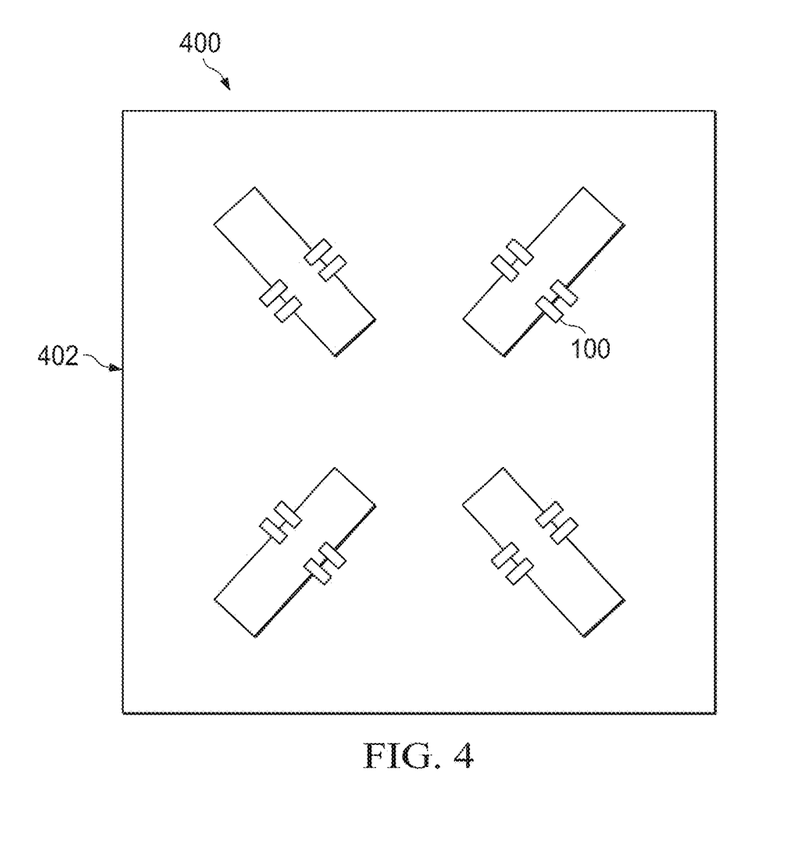
FIG. 4 illustrates an example device having multiple SAW-based hydrogel sensors for use in detecting viruses or other antigens in accordance with this disclosure.

FIG. 4 illustrates an example device 400 having multiple SAW-based hydrogel sensors 100 for use in detecting viruses or other antigens in accordance with this disclosure. In particular, FIG. 4 illustrates an example device 400 in which four sensors 100 are mounted on a common carrier 402, such as a printed circuit board. As discussed above, these sensors 100 may be coupled to a controller 206, such as via a USB or other connector. Of course, the controller 206 may also be mounted on the carrier 402 itself.

The ability to have multiple sensors 100 positioned very close to one another enables different sensors 100 to be used in different ways. For example, different sensors 100 may be functionalized with different antibodies 302 in order to detect different viruses or other antigens. As another example, different sensors 100 may be functionalized with different antibodies 302 in order to detect different mutations of the same virus. In some cases, one of the sensors 100 may be used as a reference and include inactivated antibodies 302. This reference sensor 100 may be used as a control, such as to determine when all sensors 100 need to be replaced due to water loss from their hydrogel layers 306.

Although FIG. 4 illustrates one example of a device 400 having multiple SAW-based hydrogel sensors for use in detecting viruses or other antigens, various changes may be made to FIG. 4. For example, the device 400 may include less than four or more than four sensors 100. Also, the sensors 100 may be arranged in the device 400 in any suitable manner and may or may not be placed laterally or side-by-side on a common carrier 402.

Figure 5:
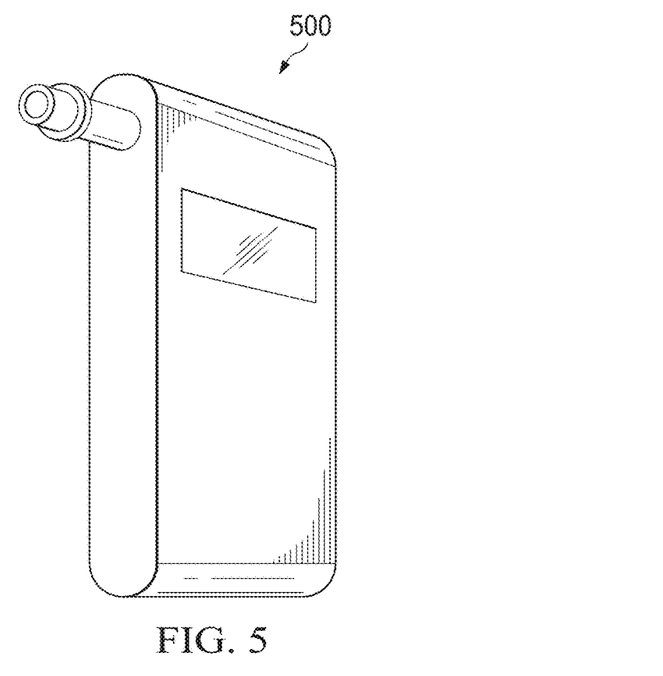
FIGS. 5 and 6 illustrate specific example devices having one or more SAW-based hydrogel sensors for use in detecting viruses or other antigens in accordance with this disclosure.
Figure 6:
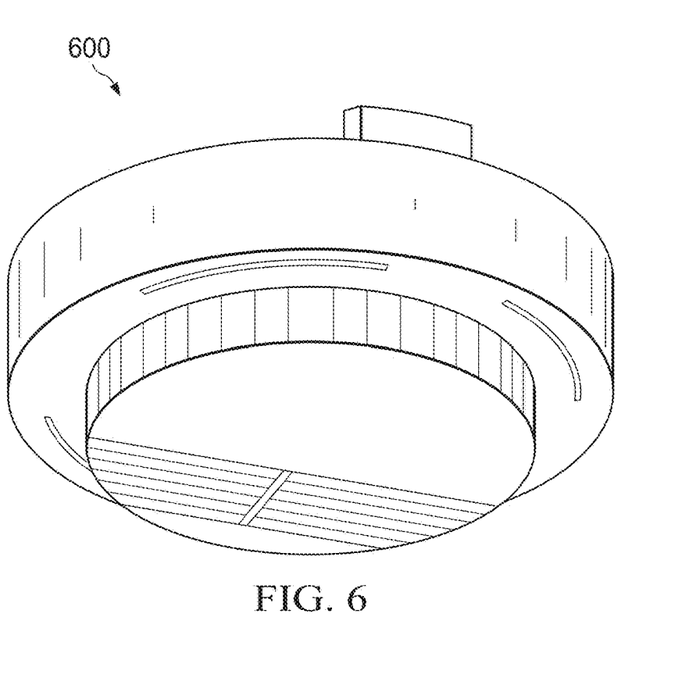

FIGS. 5 and 6 illustrate specific example devices having one or more SAW-based hydrogel sensors 100 for use in detecting viruses or other antigens in accordance with this disclosure. In particular, FIGS. 5 and 6 illustrate specific example types of devices in which one or more SAW-based sensors 100 may be used. Note, however, that the SAW-based sensors 100 may be used in any other suitable types of devices.

In FIG. 5, one or more SAW-based sensors 100 can be positioned within a handheld breathalyzer 500 or similar type of device. The breathalyzer 500 includes an input tube into which a person can blow. One or more SAW-based sensors 100 within the breathalyzer 500 can then sense whether the person's breathe includes adequate viruses or other antigens to change the frequency of the SAW-based sensor(s) 100 as described above. This type of device may be useful in various scenarios, such as when there is a need to tightly control access to a facility and prevent potentially ill personnel from entering the facility.

In FIG. 6, one or more SAW-based sensors 100 can be positioned within a wide-area monitor 600 or similar type of device. The monitor 600 can receive air within a space that might be occupied by a large number of people. One or more SAW-based sensors 100 within the monitor 600 can then sense whether the air includes adequate viruses or other antigens to change the frequency of the SAW-based sensor(s) 100 as described above. This type of device may be useful in various scenarios, such as determining whether certain locations are contaminated hot spots in which people are likely to be exposed to a virus or other antigen. Note that while this embodiment may not operate as quickly as the breathalyzer 500 to detect an infected individual (since there is not direct airflow from an individual into the monitor 600), the monitor 600 enables collective monitoring of a much larger area and a greater number of people.

Although FIGS. 5 and 6 illustrate specific examples of devices having one or more SAW-based hydrogel sensors 100 for use in detecting viruses or other antigens, various changes may be made to FIGS. 5 and 6. For example, the form factors of the devices shown here are for illustration only.

Note that while often described above as being used to detect viruses or other antigens, the approaches described above may be used to sense any biological analytes that can bind to antibodies. Also note that while often described above as being used to detect viruses or other antigens affecting people, the approaches described above can be used to sense any viruses, other antigens, or other biological analytes of interest. Thus, for example, sensors 100 may be used to detect viruses or other antigens that can affect livestock or other animals. One specific example use of the sensors 100 may be in detecting swine flu or other diseases that affect animals.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
   a surface acoustic wave (SAW) sensor comprising:
      a piezoelectric substrate;
      first and second interdigitating transistors over the piezoelectric substrate, the first interdigitating transistor configured to convert an input electrical signal into an acoustic wave, the second interdigitating transistor configured to convert the acoustic wave into an output electrical signal, the piezoelectric substrate configured to transport the acoustic wave; and
      a detection layer over the piezoelectric substrate and positioned at least partially between the first and second interdigitating transistors, the detection layer comprising (i) antibodies configured to bind to one or more biological analytes and (ii) a hydrogel layer over the antibodies;
   wherein each of the first and second interdigitating transistors comprises multiple conductive fingers; and
   wherein the detection layer extends between and into the first and second interdigitating transistors such that portions of the detection layer are positioned between the multiple conductive fingers in each of the first and second interdigitating transistors.

2. The apparatus of claim 1, wherein:
   the antibodies are configured to bind to one or more antigens; and
   the hydrogel layer is configured to permit the one or more antigens to diffuse through the hydrogel layer and contact the antibodies.

3. The apparatus of claim 1, wherein:
   the antibodies are configured to bind to one or more viruses; and
   the hydrogel layer is configured to permit the one or more viruses to diffuse through the hydrogel layer and contact the antibodies.

4. The apparatus of claim 1, wherein the hydrogel layer comprises polymer chains linked in a three-dimensional network, the hydrogel layer configured to retain water and to hydrate the antibodies.

5. The apparatus of claim 1, wherein the antibodies are configured to bind to the one or more biological analytes in order to change an oscillating frequency of the SAW sensor.

6. The apparatus of claim 5, further comprising:
   a controller configured to sense the change in the oscillating frequency of the SAW sensor.

7. The apparatus of claim 1, wherein the hydrogel layer comprises an agarose hydrogel, a polyacrylamide hydrogel, or a guar gum hydrogel.

8. The apparatus of claim 1, further comprising:
   a layer of cross-linkers attaching the antibodies to the piezoelectric substrate.

9. The apparatus of claim 1, wherein the portions of the detection layer are positioned between all of the multiple conductive fingers in each of the first and second interdigitating transistors.

10. A system comprising:
    multiple surface acoustic wave (SAW) sensors, each of the multiple SAW sensors comprising:
       a piezoelectric substrate;
       first and second interdigitating transistors over the piezoelectric substrate, the first interdigitating transistor configured to convert an input electrical signal into an acoustic wave, the second interdigitating transistor configured to convert the acoustic wave into an output electrical signal, the piezoelectric substrate configured to transport the acoustic wave; and
       a detection layer over the piezoelectric substrate and positioned at least partially between the first and second interdigitating transistors, the detection layer comprising (i) antibodies and (ii) a hydrogel layer over the antibodies;
    wherein the antibodies of at least one of the SAW sensors are configured to bind to one or more biological analytes; and
    wherein, in each of the multiple SAW sensors:
       each of the first and second interdigitating transistors comprises multiple conductive fingers; and,
       the detection layer extends between and into the first and second interdigitating transistors such that portions of the detection layer are positioned between the multiple conductive fingers in each of the first and second interdigitating transistors.

11. The system of claim 10, wherein, in the at least one of the multiple SAW sensors:
    the antibodies are configured to bind to one or more antigens; and
    the hydrogel layer is configured to permit the one or more antigens to diffuse through the hydrogel layer and contact the antibodies.

12. The system of claim 10, wherein, in the at least one of the multiple SAW sensors:
    the antibodies are configured to bind to one or more viruses; and
    the hydrogel layer is configured to permit the one or more viruses to diffuse through the hydrogel layer and contact the antibodies.

13. The system of claim 10, wherein, in each of the multiple SAW sensors, the hydrogel layer comprises polymer chains linked in a three-dimensional network, the hydrogel layer configured to retain water and to hydrate the antibodies.

14. The system of claim 10, wherein, in the at least one of the multiple SAW sensors, the antibodies are configured to bind to the one or more biological analytes in order to change an oscillating frequency of the SAW sensor.

15. The system of claim 14, further comprising:
at least one controller configured to sense the Change in the oscillating frequency of the at least one of the multiple SAW sensors.

16. The system of claim 10, wherein, in at least one other of the multiple SAW sensors, the antibodies are inactivated.

17. The system of claim 10, wherein, in each of the multiple SAW sensors, the portions of the detection layer are positioned between all of the multiple conductive fingers in each of the first and second interdigitating transistors.

18. The system of claim 10, wherein:
at least two of the multiple SAW sensors include different antibodies; and
at least one of:
the different antibodies are configured to bind to different viruses; and
the different antibodies are configured to bind to different mutations of a virus.

19. A method comprising:
providing a flow of air to one or more surface acoustic wave (SAW) sensors; and
detecting one or more biological analytes in the flow of air using the one or more SAW sensors;
wherein at least one of the one or more SAW sensors comprises:
a piezoelectric substrate;
first and second interdigitating transistors over the piezoelectric substrate, the first interdigitating transistor configured to convert an input electrical signal into an acoustic wave, the second interdigitating transistor configured to convert the acoustic wave into an output electrical signal, the piezoelectric substrate configured to transport, the acoustic wave; and
a detection layer over the piezoelectric substrate and positioned at least partially between the first and second interdigitating transistors, the detection layer comprising (i) antibodies configured to bind to the one or more biological analytes and (ii) a hydrogel layer over the antibodies; and
wherein, in each of the one or more SAW sensors:
each of the first and second interdigitating transistors comprises multiple conductive fingers; and
the detection layer extends between and into the first and second interdigitating transistors such that portions of the detection layer are positioned between the multiple conductive fingers in each of the first and second interdigitating transistors.

20. The method of claim 19, further comprising:
detecting different biological analytes in the flow of air using different SAW sensors, the different SAW sensors comprising different antibodies.

* * * * *